(12) United States Patent
Hamasaki et al.

(10) Patent No.: US 11,273,129 B2
(45) Date of Patent: Mar. 15, 2022

(54) PARTICLE COMPOSITION FOR EASY-TO-USE SOLID PREPARATION AND EASY-TO-USE SOLID PREPARATION INCLUDING SAID PARTICLE COMPOSITION

(71) Applicant: DAICEL CORPORATION, Osaka (JP)

(72) Inventors: Momoko Hamasaki, Himeji (JP); Tomohito Okabayashi, Himeji (JP); Anan Sakaguchi, Himeji (JP); Takahiro Hiramura, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 0 days.

(21) Appl. No.: 15/760,854

(22) PCT Filed: Sep. 21, 2016

(86) PCT No.: PCT/JP2016/077883
§ 371 (c)(1),
(2) Date: Mar. 16, 2018

(87) PCT Pub. No.: WO2017/057147
PCT Pub. Date: Apr. 6, 2017

(65) Prior Publication Data
US 2019/0110998 A1 Apr. 18, 2019

(30) Foreign Application Priority Data

Sep. 30, 2015 (JP) ................................ 2015-192777
Jan. 13, 2016 (JP) ............................. JP2016-004123
Apr. 13, 2016 (JP) ................................ 2016-080488

(51) Int. Cl.
| | | |
|---|---|---|
| *A61K 9/28* | (2006.01) | |
| *A23L 5/00* | (2016.01) | |
| *A61K 9/50* | (2006.01) | |
| *A61K 9/20* | (2006.01) | |
| *A61K 9/16* | (2006.01) | |
| *A23L 29/269* | (2016.01) | |
| *A23P 20/10* | (2016.01) | |
| *A23P 10/22* | (2016.01) | |
| *A23L 29/262* | (2016.01) | |
| *A23P 10/28* | (2016.01) | |
| *A23L 29/256* | (2016.01) | |
| *A23L 33/125* | (2016.01) | |

(52) U.S. Cl.
CPC .................... *A61K 9/28* (2013.01); *A23L 5/00* (2016.08); *A23L 29/256* (2016.08); *A23L 29/262* (2016.08); *A23L 29/27* (2016.08); *A23L 33/125* (2016.08); *A23P 10/22* (2016.08); *A23P 10/28* (2016.08); *A23P 20/105* (2016.08); *A61K 9/1652* (2013.01); *A61K 9/2054* (2013.01); *A61K 9/2826* (2013.01); *A61K 9/2866* (2013.01); *A61K 9/5047* (2013.01); *A23V 2002/00* (2013.01)

(58) Field of Classification Search
None
See application file for complete search history.

(56) References Cited

U.S. PATENT DOCUMENTS

| | | |
|---|---|---|
| 6,264,989 B1 | 7/2001 | Kato et al. |
| 2001/0033864 A1 | 10/2001 | Colonno et al. |
| 2004/0068014 A1* | 4/2004 | Sakai .................. A61K 31/196 514/567 |
| 2012/0082723 A1 | 4/2012 | Kudou et al. |

FOREIGN PATENT DOCUMENTS

| | | |
|---|---|---|
| EP | 2 042 164 | 4/2009 |
| EP | 2 412 386 | 2/2012 |
| JP | S56100801 | 8/1981 |
| JP | 9-104621 | 4/1997 |
| JP | 2009203559 | 9/2009 |
| JP | 2012-255017 | 12/2012 |
| JP | 2015155386 | 8/2015 |
| TW | 200637499 | 11/2006 |
| WO | 99-20745 | 4/1999 |
| WO | 2006062089 | 6/2006 |
| WO | 2007-148786 | 12/2007 |
| WO | 2010-110321 | 9/2010 |
| WO | 2010-260803 | 11/2010 |
| WO | 2011125798 | 10/2011 |

(Continued)

OTHER PUBLICATIONS

Yasuo (JP 2015155386 English translation) (Year: 2015).*
Kuduo et al. (WO 2011125798 A1 English translation) (Year: 2011).*
Akimoto (WO 2006062089 A1 English translation) (Year: 2006).*
International Search Report and Written Opinion of International Searching Authority of International Application No. PCT/JP2016/077883 dated Nov. 1, 2016.
Supplementary European Search Report of Application No. EP 16 85 1321 dated May 17, 2019.

*Primary Examiner* — Quanglong N Truong
(74) *Attorney, Agent, or Firm* — Xsensus LLP

(57) ABSTRACT

An object of the present invention is to provide a particulate composition for an easy-to-take solid preparation, which has excellent moldability (hardness) and slipperiness.

The present invention relates to a particulate composition for an easy-to-take solid preparation, comprising sugar alcohol and a gelling agent that will show slipperiness when it is brought into contact with water, wherein a part or whole of the surface of the particulate composition is coated with the gelling agent, to an easy-to-take solid preparation comprising the particulate composition, and to a method for the production of the easy-to-take solid preparation.

16 Claims, 1 Drawing Sheet

(56) References Cited

FOREIGN PATENT DOCUMENTS

WO  2012-075455  6/2012

* cited by examiner

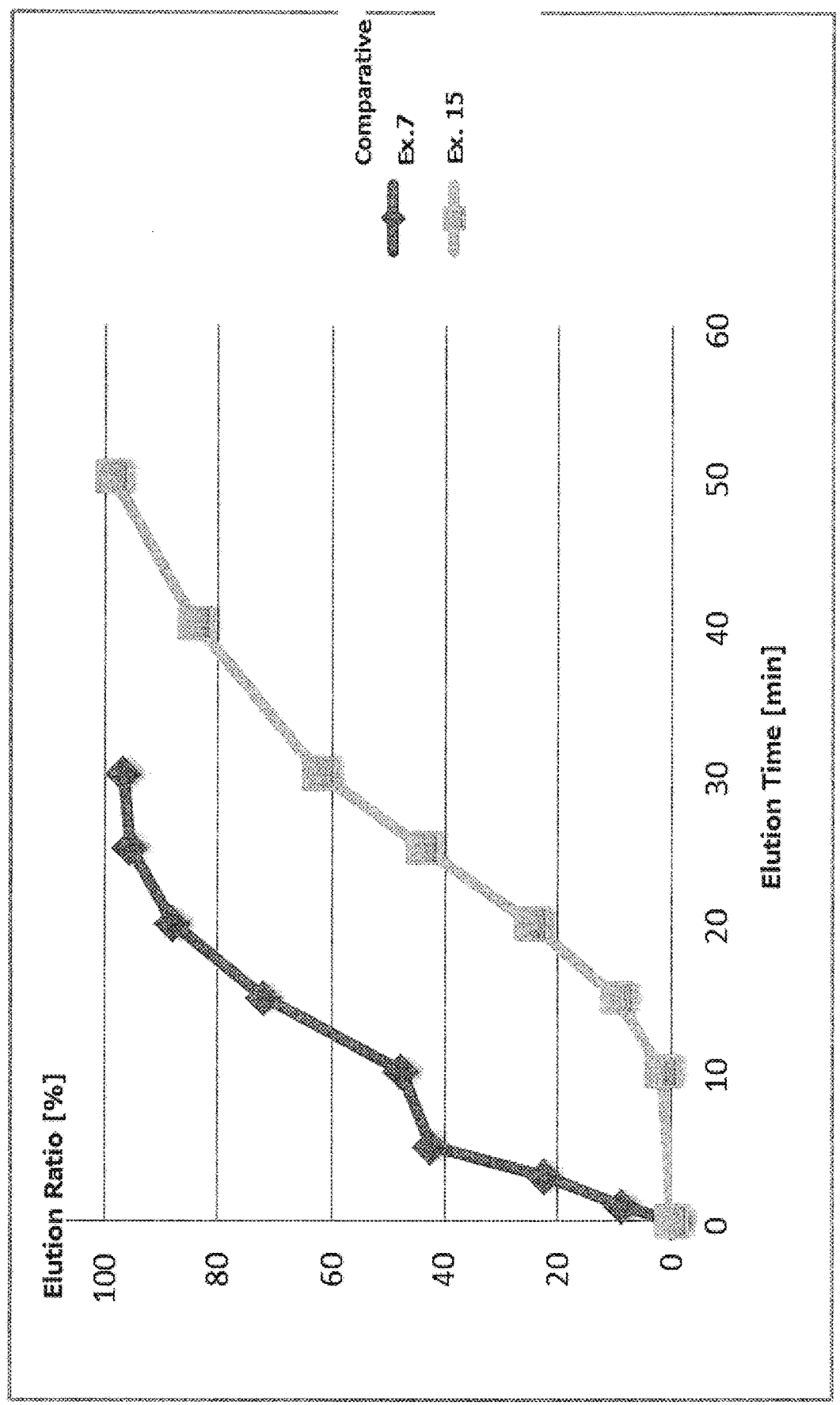

PARTICLE COMPOSITION FOR EASY-TO-USE SOLID PREPARATION AND EASY-TO-USE SOLID PREPARATION INCLUDING SAID PARTICLE COMPOSITION

TECHNICAL FIELD

The present invention relates to a particulate composition for an easy-to-take solid preparation, comprising sugar alcohol and a gelling agent that will show slipperiness when it is brought into contact with water, wherein a part or whole of the surface of the particulate composition is coated with the gelling agent, an easy-to-take solid preparation comprising the particulate composition and the like. The particulate composition preferably comprises a water-insoluble polymer.

BACKGROUND ART

Taking properties of a preparation for oral administration have been previously improved for patients who have difficulty in swallowing, elderly people and children who have a weak swallowing ability and the like. For example, the preparations are formulated into liquid or jelly preparation form in many cases. However, when a content of a main drug is high, it will be difficult to mask its taste. And, when an active ingredient such as a drug is unstable in water, it will be difficult to be formulated in any preparation form.

Accordingly, easy-to-take preparations have been recently developed for facilitating swallowing of the solid preparation, wherein the surface of the preparations is coated with a gelling agent so that they will show slipperiness and become slippery against mucous membrane and easy to swallow when they are brought into contact with water in oral cavity.

These techniques use processes such as, for example, 1) formulating gell into a tablet by freeze-drying of; 2) punching into a circle shape a film of gelling layers comprising a drug layer between them; 3) punching into a circle shape gelling film layers comprising a tablet between them; 4) spraying a coating solution for gelling on a tablet, and the like.

Patent Literature (PTL) 1 discloses a coating composition for use in an easy-to-take solid preparation, which comprises a first thickener of a metal-crosslinking thickener, a polyvalent metal compound, and a second thickener; a method for the production of a preparation for oral administration by spray-coating alcohol solution having the coating composition dispersed therein onto a drug core comprising an active ingredient; and the preparation for oral administration produced thereby.

Patent Literature (PTL) 2 discloses 100% erythritol spherical particulate for a direct compression, which is obtained by granulating under spraying of ethanol, drying and grading 100% erythritol ultra-fine powder in a range of from 0.4 μm to 23 μm of an average diameter for the purpose of providing the 100% erythritol spherical particulate.

Patent Literature (PTL) 3 discloses a method for the production of an excipient for use in compression processing for foods and pharmaceuticals, which comprises spraying and granulating aqueous solution of sugar alcohol by means of a fluidized-bed granulation coating device to obtain assembly of granulated sugar alcohol without formulating a binder.

However, none of these patent documents discloses a particulate composition for compression-molding of a solid preparation in a dry process, comprising sugar alcohol and a gelling agent that will show slipperiness when it is brought into contact with water, or an easy-to-take solid preparation comprising the particulate composition.

RELATED ARTS

Patent Literatures

PTL 1: International Publication Pamphlet WO2011/125798
PTL 2: JP-A-2014-210746
PTL 3: Japanese Patent No. 3491887
PTL 4: JP-A-Sho56 (1981)-100801
PTL 5: JP-A-2009-203559

SUMMARY OF INVENTION

Problems to be Solved by the Invention

The conventional treatment with a gelling agent seen in the prior arts such as PTL 1 was complicated since it requires the preparation of a gelling agent solution, the transfer to a coating machine after the compression molding and the like. Furthermore, a functional or active ingredient cannot be used if their stability for a solvent used in these processes is low. There has been a problem that it was difficult to form a thick coating layer when the gelling agent was coated.

The erythritol spherical particulate for direct compression disclosed in PTL 2 of will need an organic solvent, and it will also require the addition of other additives in order to obtain a desired tablet hardness since formability of the resulting particulate is low.

The method disclosed in PTL 3 has problems such as that the granulating conditions need to be controlled strictly and that a rotary container is required since a usual fluidized-bed granulation would generate aggregation and fixing of the sugar alcohol.

Accordingly, an object of the present invention is to solve such technical problems in the arts, and to provide the particulate composition for an easy-to-take solid preparation, which has excellent moldability (hardness) and slipperiness that are useful for the solid preparation; and the easy-to-take solid preparation comprising the composition. The term "easy-to-take" generally means "easy to drink" or "easy to swallow", as the characteristics or property of the solid preparations and the like.

Another object of the present invention is to provide a method for the production of the easy-to-take solid preparation, comprising only a step of compression-molding the particulate composition in a dry process.

None of the above Patent Literatures discloses or suggests such technical problems.

Means to Solve the Problem

The present inventors have earnestly studied to solve the above problems and completed the invention comprising the following aspects Thus, the present invention provides the following aspects.

[Aspect 1]

A particulate composition for an easy-to-take solid preparation, comprising sugar alcohol and a gelling agent that will show slipperiness when it is brought into contact with water, wherein a part or whole of the surface of the particulate composition is coated with the gelling agent.

[Aspect 2]
The particulate composition according to Aspect 1, further comprising a water-insoluble polymer.
[Aspect 3]
The particulate composition according to Aspect 3, wherein the water-insoluble polymer is micro-fibrillated cellulose.
[Aspect 4]
The particulate composition according to Aspect 3, wherein the micro-fibrillated cellulose has an average fiber length of 0.01-2 mm, and an average fiber diameter of 0.001-1 μm.
[Aspect 5]
The particulate composition according to Aspect 2, wherein the water-insoluble polymer is crystalline cellulose.
[Aspect 6]
The particulate composition according to any one of Aspects 1-5, wherein the sugar alcohol comprises one or more selected from the group consisting of erythritol, xylitol, mannitol, sorbitol, lactitol, isomalt and maltitol.
[Aspect 7]
The particulate composition according to any one of Aspects 1-6, wherein the gelling agent comprises at least one kind of a water-soluble polymer.
[Aspect 8]
The particulate composition according to Aspect 7, wherein the water-soluble polymer is selected from the group consisting of sodium carmellose, xanthan gum, sodium alginate, carrageenan, guar gum and gelatin.
[Aspect 9]
The particulate composition according to Aspect 2, comprising the sugar alcohol selected from the group consisting of erythritol, xylitol, isomalt and mannitol; the water-insoluble polymer that is the micro-fibrillated cellulose or the crystalline cellulose; and sodium carmellose.
[Aspect 10]
The particulate composition according to any one of Aspects 1-9, which is used as an outer layer of the easy-to-take solid preparation.
[Aspect 11]
A method for the production of the particulate composition according to any one of Aspects 1-10, comprising a step of spraying a liquid comprising the gelling agent that will show slipperiness when it is brought into contact with water to a composition comprising at least the sugar alcohol.
[Aspect 12]
A method for the production of the particulate composition according to any one of Aspects 1-10, comprising a step of investing powder of the gelling agent that will show slipperiness when it is brought into contact with water into a composition comprising at least the sugar alcohol, so that a part or whole of the surface of the particulate (composition) is coated with the gelling agent.
[Aspect 13]
An easy-to-take solid preparation comprising the particulate composition according to Aspects 1-10, or the particulate composition obtained by the method for the production according to Aspect 11 or 12.
[Aspect 14]
An easy-to-take solid preparation for foods or pharmaceuticals, wherein an inner core is coated with the outer layer consisting of the particulate composition according to Aspects 1-10, or the particulate composition obtained by the method for the production according to Aspect 11 or 12.

[Aspect 15]
A method for the production of the easy-to-take solid preparation according to any one of Aspects 13-14, comprising only a step of compression-molding in a dry process.

Advantages of Invention

The present invention provides the particulate composition that has the excellent moldability (hardness) and is useful as the particulate composition for an outer layer of the easy-to-take solid preparation and the like, so that the intercalation between an inner layer (inner core) and the outer layer of the solid preparation can be inhibited. Furthermore, the present invention makes it possible to increase thickness of the outer layer of the preparation so as to increase easiness to swallow, and increase a masking effect for the taste of a core tablet.

Furthermore, since a part or whole of the surface of the particulate (composition) is coated with the gelling agent, deviation in the distribution of the gelling agent can be reduced. As a result, as a sufficient slipperiness can be demonstrated by the addition of a relatively small amount of the gelling agent, the particulate composition is preferably applied to the easy-to-take solid preparation for various kinds of foods.

Furthermore, it is possible to produce the easy-to-take solid preparation by using the above particulate composition without going through any wet condition, functional or active ingredients can be used even if their stability in a solvent is low.

[FIG. 1] shows the results of elution test of the tablets obtained Example 15 and Comparative Example 7.

EMBODIMENTS FOR CARRYING OUT THE INVENTION

A first aspect of the present invention relates to the particulate composition for the easy-to-take solid preparation, comprising sugar alcohol and the gelling agent that will show slipperiness when it is brought into contact with water, wherein apart or whole of the surface of the particulate (composition) is coated with the gelling agent. As shown by the Examples, the particulate composition shows excellent moldability and slipperiness.

The sugar alcohol may be any one known for those skilled in the art such as one or more selected from the group consisting of erythritol, xylitol, mannitol, sorbitol, lactitol, isomalt and maltitol.

The gelling agent that will show slipperiness when it is brought into contact with water according to the present invention means a material that will form a slippery surface of a solid tablet under the moisture condition in an oral cavity when it is taken without water so as to promote the slipperiness of the tablet itself. Such promotion of the slipperiness of the tablet will also make it easy to swallow the tablet even when it is taken with water.

The representative examples of the water-soluble polymer comprised in the gelling agent include the water-soluble polymer that is selected from the group consisting of sodium carboxylmethylcellulose (also, called "sodium carmellose"), xanthan gum, sodium alginate, carrageenan, guar gum and gelatin. The water-soluble polymer may be naturally-occurring or synthetic one.

It is preferable to incorporate the water-insoluble polymer into the particulate composition for the easy-to-take solid preparation according to the present invention in order to effectively increase its moldability. Any materials known to those skilled in the art can be used as long as it can accomplish the purpose of the water-insoluble polymer, which may be naturally-occurring or synthetic one.

Preferable examples of the water-insoluble polymer include micro-fibrillated cellulose, crystalline cellulose, powdered cellulose and various kinds of cellulose derivatives. The micro-fibrillated cellulose and crystalline cellulose are more preferred among them.

The micro-fibrillated cellulose is generally produced from the vegetable fiber and having the fiber diameter (the short diameter) or thickness of from about a few nm to 1 μm. The surface area of the micro-fibrillated cellulose has been increased, its hydrophilic property that is the original characteristics of cellulose has been significantly strengthened, and its three-dimensional network has been formed, without deteriorating the basic properties such physical and chemical stabilities of the starting material of cellulose.

A dry material of the micro-fibrillated cellulose may be directly obtained in a dry state by any method known in the art, such as by directly pulverizing cellulose fiber in a dry state with a ball mill (PTL 4). Alternatively, the dry material of the micro-fibrillated cellulose may be obtained by subjecting the micro-fibrillated cellulose suspended in water, which was prepared by micro-fibrillation of water-dispersion of the cellulose fiber with a high-pressure homogenizer, to a solvent displacement stage, and removing the solvent in a drying stage, followed by pulverization in a pulverizing stage (PTL 5).

Preferable examples of the micro-fibrillated cellulose include fiber assembly that has an average fiber length of 0.01~2 mm and an average fiber diameter of 0.001~1 μm, preferably of 0.01~0.1 μm. For example, such micro-fibrillated cellulose (a solid content of 10~35% in water) is commercially available with a trade name of "CELISH" series with various grades (an average fiber diameter of 0.01~0.1 μm) from Daicel FineChem Ltd.

Representative examples of the crystalline cellulose include commercially-available products such as "Avicel" (FMC Corporation), "CEOLUS" (Asahi Kasei Chemicals Corp.), and "VIVAPUR" (RETTENMAIER) can be mentioned. Representative examples of the powdered cellulose include KC Flock (NIPPON PAPER Chemicals CO., LTD) and ARBOCEL (RETTENMAIER) and Solka Flock (Kimura Sangyo Co., Ltd.) and the like.

The particulate composition for the easy-to-take solid preparation according to the present invention is characterized by that apart or whole of its surface is coated with the gelling agent. The thickness of a coating layer of the gelling agent is not necessary to be uniform over the whole of the coating layer. The composition inside of the coating layer of the gelling agent comprises at least the sugar alcohol and preferably the water-insoluble polymer. The gelling agent may be comprised in the composition inside of the coating layer.

Although a mixing ratio of the components of the particulate composition, the sugar alcohol, the water-insoluble polymer and the gelling agent that will show slipperiness when it is brought into contact with water may be optionally selected by those skilled in the art, being usually 50-99% by weight, 0-30% by weight and 0.01-30% by weight, respectively, and preferably 60-99% by weight, 1-20% by weight and 0.05-20% by weight. The ratio of the coating layer of the gelling agent usually amounts to 0.01-20% by weight, preferably to 0.05-10% by weight of the total of the particulate composition. The particulate composition may further comprise other components.

It is preferable that the particulate composition of the present invention has the following physical properties:

(1) an average particle size of 50 to 500 microns; and
(2) a water content of 0.1% to 10.0% by weight.

The particulate composition for the easy-to-take solid preparation according to the present invention may be produced by any method or means known in the art as described in the Examples. Accordingly, the particulate composition may take various structures (or layer structures). For example, as provided as a second aspect of the present invention, the particulate composition having the coating layer of the gelling agent may be produced by spraying a liquid comprising the gelling agent that will show slipperiness when it is brought into contact with water to a composition comprising at least the sugar alcohol and preferably the water-insoluble polymer.

The composition coated with the coating layer of the gelling agent may also be produced by any method or means known in the art.

Thus, as described in the Examples, the liquid comprising the gelling agent may be sprayed onto the (inside) composition comprising at least the sugar alcohol and preferably the water-insoluble polymer, or onto an inside granulate comprising the particulate composition and the gelling agent. Alternatively, a liquid comprising the water-insoluble polymer is sprayed onto an inside granulate comprising the sugar alcohol and the gelling agent so as to provide a coating layer (inside) of the water-insoluble polymer, and the liquid comprising the gelling agent is sprayed onto the above coating layer (inside) to provide the coating layer of the gelling agent outside of the coating layer of the water-insoluble polymer.

Instead of spraying the liquid comprising the gelling agent, the particulate composition the part or whole of the surface of which is coated with the gelling agent may be produced by investing the powder of the gelling agent into the composition comprising at least the sugar alcohol and preferably the water-insoluble polymer, while spraying water onto the composition.

Furthermore, a third aspect of the present invention relates to the easy-to-take solid preparation comprising the particulate composition according to the present invention. The particulate composition can be comprised in the solid preparation as any constituent or in any form. For example, the particulate composition of the present invention is comprised as an excipient in the solid preparation. The particulate composition may be used as an outer layer of the easy-to-take solid preparation, which will therefore form the easy-to-take solid preparation wherein an inner core (tablet) is coated with the particulate composition according to the present invention.

A specific example of the easy-to-take solid preparation according to the present invention is one for foods or pharmaceuticals.

The easy-to-take solid preparation according to the present invention may be produced by any means or method known for those skilled in the art, especially by the production method described below.

Thus, there may be listed a dry compression-molding method for the production of the easy-to-take solid preparation wherein the inner core tablet is coated with a compression-molded outer layer-forming agent (the outer layer), comprising loading separately or simultaneously the inner core tablet and powder of the particulate composition to a mortar inner surface, the bottom end surface of an upper-pestle, and the top end surface of a lower-pestle, and subsequently compression-molding them. The inner core tablet may be prepared using a core-molding material by any means or method known for those skilled in the art, preferably being obtained by compression-molding the core-molding material in the dry process. The powder of the particulate composition may be loaded after a lubricant has been applied to the mortar inner surface, and the surfaces of the upper-pestle and the lower-pestle.

The "powder" in the above method means the aggregate of solid particulates, which may include powder having finer size or shape than granules or grains. The ingredients comprised in the powder of the particulate composition for the outer layer and the core-molding material may be used as they are, or the powder of the particulate composition for the outer layer-forming agent and the core-molding material may be prepared by any means or method known in the art such as a dry granulation process, a wet granulation process and the like.

The dry granulation process includes crushing granulation and roll-compressing method, comprising the steps of compressing each powder components into small bulks with a pressure, and appropriately crushing and granulating them, for example.

On the other hand, the wet granulation process is a method in which each component is dispersed in the presence of water, and the dispersion is dried to form complexes. As specific examples of the wet granulation process, spray methods such as spray drying, tumbling granulation, agitation granulation and fluidized-bed granulation; freeze-drying method; kneading granulation, and the like can be mentioned. They can be produced by any of these methods known to a person skilled in the art.

In the method according to the present invention, the mortar, the upper-pestle, and the lower-pestle are a member for compressing the inner core tablet and the outer layer-forming agent along the four directions, so as to mold the easy-to-take solid preparation wherein the compression-molded inner core tablet is coated with the particulate composition for the outer layer. They comprise any other members that are named differently in any other powder compression-molding machines or devices as long as they have substantially the same functions and/or properties as the above ones.

Each process of loading the inner core tablet and the powder of the particulate composition for the outer layer to the mortar inner surface, the bottom end surface of the upper-pestle, and the top end surface of the lower-pestle, etc. may be performed by any means or method known for those skilled in the art depending on the production machine used and the like. For example, the loading of the inner core tablet and the powder of the particulate composition for the outer layer to the mortar inner surface, the bottom end surface of the upper-pestle, and the top end surface of the lower-pestle may be simultaneously or separately carried out by using any appropriate means, or the powder of the particulate composition for the outer layer may be loaded repeatedly a few times. For example, the powder of the particulate composition for the outer layer is loaded, followed by the loading of the inner core tablet, and then followed by the loading of the powder of the particulate composition for the outer layer again. Furthermore, compression-molding of the inner core tablet and the powder of the particulate composition for the outer layer may be carried out all at once.

The easy-to-take solid preparation according to the present invention has uses, for example, as various foods such as supplemental foods, nutrition function foods and health foods; and as pharmaceuticals.

The easy-to-take solid preparation, especially the core-molding material in the above method may therefore optionally comprise various components known for those skilled in the art depending on the above uses.

For use as the foods, for example, it may comprise various nutritional components such as proteins, carbohydrates, lipids and minerals; components for health foods such as various extracts from microorganisms, plants and animals; various vitamins and their derivatives; and designated or existing additives according to Food Sanitation Law, Art. 10; and other components acceptable as a food component (a food additive) listed in a list of general additives for food and drink, such as acidulants, sweeteners, excipients, surfactants, lubricants, auxiliary agents, corrigents, flavoring agents, colorants, and stabilizing agents.

For use as the pharmaceuticals, for example, it may comprise in addition to a medicinal or active ingredient, other any pharmaceutically acceptable components, such as excipients, surfactants, lubricants, auxiliary agents, acidulants, sweeteners, corrigents, flavoring agents, colorants, and stabilizing agents, when needed. As these optional components, for example, appropriate ingredients described in "Japanese Pharmaceutical Excipients Directory" (YAKUJI NIPPO LIMITED) or the Japanese Pharmacopoeia; designated or existing additives according to Food Sanitation Law, Art. 10; natural flavor; and additives listed in a list of general additives for food and drink can be used. There is no limitation in the kind of the medicinal ingredient and the above auxiliaries. Also, the blending ratios of each optional ingredient (component) are not particularly limited as long as the desired effects of the present invention are brought about, and the blending ratios can properly be determined by those skilled in the art.

There is no limitation on an application or kind of the medicinal ingredients, which may include, for example, agents affecting each organ such as the central nervous system, peripheral nervous system, a sensory organ, a circulatory organ, a respiratory organ and a digestive organ and an urogenital organ; hormone drug; agents affecting metabolism such as a vitamin drug, an analeptic, an agent affecting blood and body fluid; agents affecting the function of tissue and cell such as an agent activating cellular function, an agent affecting tumors, an radioactive medicine, an anti-allergic agent; medicines based on a medical prescription relating to herbal medicines and Chinese medicines; antibiotics; agents for chemotherapy, biological drug; agents for pathogenic organisms such as parasites; agents for formulation use, diagnosis, public health and in-vitro diagnosis.

Those skilled in the art may optionally select the various conditions in the processes of the production method according to the present invention, such as pressure and time of the compression-molding, amounts of the particulate composition for the outer layer and the core-molding material, and the size and shape of the inner core tablet, depending on the scale and kind of the machine to be used in the method, the size and application of a desired easy-to-take solid preparation and the like. For example, tablet compression force in the compression-molding usually ranges from 2 to 100 kN.

There is no limitation on the size, shape and the like of the solid preparation according to the present invention. It is usually within a range of from 3 to 20 mm in diameter and of from 15 to 2000 mg in weight. And, the inner core tablet usually has a diameter with a range of from 1.8 to 18 mm and a weight with a range of from 10 to 1800 mg. They may have any shape known for those skilled in the art such as those of a flat with bevel-edge tablet and a truly-flat tablet. The thickness of the outer layer (coating) consisting of the particulate composition for the outer layer ranges from about 0.1 to about 5 mm. These values can be determined by any method known for those skilled in the art.

In addition, contents of all related art documents cited in the present specification are incorporated herein by reference.

EXAMPLES

Hereinafter, the present invention will be more specifically described with reference to Examples. However, the present invention is not considered to be limited to the Examples.

[Evaluation on an Average Diameter of the Particulate, Water Content, Hardness, Slipperiness, Taste-Masking Effect, Elution Time, and Abrasion Degree]

The tablets obtained in the Examples and Comparative Example were measured based on the following conditions/methods with respect to an average diameter of the particulate, water content, hardness, slipperiness, taste-masking effect, elution time, and abrasion degree.

Average particle diameter: 2 g of the disintegrative particulate composition is subjected to a measurement with a Φ75 mm automatic shaking sieve device (Type "M-2", Tsutsui Scientific Instruments Co., Ltd.).

Water content: 5 g of the particulate composition is subjected to a measurement using a halogen water content measuring device (Type "HB43", METTLER TOLEDO K.K.).

Hardness: Hardness (N) was measured with a digital Kiya hardness tester (Fujiwara Scientific Company Co., Ltd.). The measurement for the hardness was repeated six times for each tablet, and an average value thereof was regarded as a measurement result.

Slipperiness: After a Φ8 mm or Φ12 mm tablet is loaded into a silicon tube having an inner diameter of 7 mm and an outer diameter of 10 mm, or having an inner diameter of 10 mm and an outer diameter of 12 mm, respectively, water is added so that slipperiness can appear. The silicon tube is then pinched with a jig above the tablet, and the pinched silicon tube is then pulled upwards at a rate of 1 mm/sec so as to make the tablet move in the silicon tube. A stress during the moving of the tablet in the silicon tube at the rate of 1 mm/sec is then measured by means of Texture Analyzer (TA, XT plus, Stable Micro Systems). The lower the measured stress is, the better the slipperiness of the tablet is.

Taste-masking effect: Five men and women, respectively took the tablet without water, and an average time until which the taste of vitamin C could not be felt was regarded as a measurement result.

Elution time: It is measured according to "Elution Test" (a paddle method) described in the Japanese Pharmacopoeia, using water as an eluate. Elution ratio of vitamin C into the eluate is measured according to Ultraviolet-Visible Spectrophotometry. Thus, the absorbance of a test liquid measured at 243 nm is compared to the absorbance of a standard solution at 243 nm that has been prepared by dissolving vitamin C (Eisai Food Chemicals) at substantially the same concentration as that of vitamin C comprised in the eluate.

Abrasion degree: It is measured according to "Method of Abrasion Degree of a Tablet" described in the Japanese Pharmacopoeia.

Comparative Example 1

[Production of the Particulate Composition 1]

368 g of erythritol (Erythritol T, Mitsubishi-Chemical Foods Corporation) was charged to a fluidized-bed granulator (FL-LABO, Freund Corporation), and 640 g of 5% suspension of wet material of micro-fibrillated cellulose ("CELISH", Daicel FineChem Ltd.) in water was sprayed onto it at a rate of 12 g/minute for granulation to thereby obtain particulate composition 1. The resulting particulate composition 1 had the following values for physical properties: (1) an average particle size of 165 microns and (2) a water content of 0.53% by weight.

The resulting particulate composition 1 was then subjected to tableting at a tablet compression force of 8 kN with a simple tableting machine (HANDTAB-100, ICHIHASHI-SEIKI Co., Ltd.) to thereby obtain a tablet having a diameter of 8.0 mm, R6.5 and a weight of 200 mg.

Comparative Example 2

9.92 g of the particulate composition obtained in Comparative Example 1 and 0.08 g of sodium carmellose (CMC Daicel, Daicel FineChem Ltd.) were mixed to obtain a composition. The resulting composition was then subjected to tableting at a tablet compression force of 8 kN with the simple tableting machine (HANDTAB-100, ICHIHASHI-SEIKI Co., Ltd.) to thereby obtain a tablet having a diameter of 8.0 mm, R6.5 and a weight of 200 mg, wherein a small amount of calcium stearate (Taihei Chemical Industrial Co. Ltd.) had been applied in advance to a mortar inner surface, and the surfaces of an upper-pestle and a lower-pestle in the above tableting machine.

Example 1

Production of the Particulate Composition 2

396.8 g of the particulate composition obtained in Comparative Example 1 was charged to the fluidized-bed granulator (FL-LABO, Freund Corporation), and 320 g of an aqueous solution of sodium carmellose (CMC Daicel, Daicel FineChem Ltd.) at 1% by weight was sprayed onto it at a rate of 5 g/minute for granulation to thereby obtain a particulate composition 2 according to the present invention. The resulting particulate composition 2 had the following values for physical properties: (1) an average particle size of 180 microns and (2) a water content of 0.81% by weight.

The resulting particulate composition 2 was then subjected to tableting at a tablet compression force of 8 kN with the simple tableting machine (HANDTAB-100, ICHI-HASHI-SEIKI Co., Ltd.) to thereby obtain a tablet having a diameter of 8.0 mm, R6.5 and a weight of 200 mg.

Example 2

Production of the Particulate Composition 3

380.0 g of the particulate composition obtained in Comparative Example 1 and 16.8 g of sodium carmellose (CMC Daicel, Daicel FineChem Ltd.) were charged to the fluidized-bed granulator (FL-LABO, Freund Corporation), and 320 g of an aqueous solution of sodium carmellose (CMC Daicel, Daicel FineChem Ltd.) at 1% by weight was sprayed onto it at a rate of 5 g/minute for granulation to thereby obtain a particulate composition 3 according to the present invention. The resulting particulate composition 3 had the following values for physical properties: (1) an average particle size of 307 microns and (2) a water content of 1.45% by weight.

The resulting particulate composition 3 was then subjected to tableting at a tablet compression force of 8 kN with the simple tableting machine (HANDTAB-100, ICHI-HASHI-SEIKI Co., Ltd.) to thereby obtain a tablet having a diameter of 8.0 mm, R6.5 and a weight of 200 mg. The abrasion degree of the resulting tablet was measured to be 0.02%, showing that the tablet produced using the particulate composition 3 had little abrasion and was excellent in physical hardness.

Example 3

Production of the Particulate Composition 4

353.4 g of erythritol (Erythritol T, Mitsubishi-Chemical Foods Corporation) and 16.8 g of sodium carmellose (CMC Daicel, Daicel FineChem Ltd.) were charged to the fluidized-bed granulator (FL-LABO, Freund Corporation). 532 g of 5% suspension of wet material of micro-fibrillated cellulose ("CELISH", Daicel FineChem Ltd.) in water was sprayed onto it at a rate of 12 g/minute and then 320 g of an aqueous solution of sodium carmellose (CMC Daicel, Daicel FineChem Ltd.) at 1% by weight was sprayed onto it at a rate of 5 g/minute for granulation to thereby obtain particulate composition 4 according to the present invention. The resulting particulate composition 4 had the following values for physical properties: (1) an average particle size of 323 microns and (2) a water content of 1.37% by weight.

The resulting particulate composition 4 was then subjected to tableting at a tablet compression force of 8 kN with the simple tableting machine (HANDTAB-100, ICHI-HASHI-SEIKI Co., Ltd.) to thereby obtain a tablet having a diameter of 8.0 mm, R6.5 and a weight of 200 mg.

In the following Examples 4 to 6, another water-soluble polymer was used in addition to sodium carmellose used in Example 3 to produce the particulate compositions according to the present invention.

Example 4

Production of the Particulate Composition 5

350.6 g of erythritol (Erythritol T, Mitsubishi-Chemical Foods Corporation) and 19.9 g of i-carrageenan (Carrageenan MV 512, Mitsubishi-Chemical Foods Corporation) were charged to the fluidized-bed granulator (FL-LABO, Freund Corporation). 558 g of 5% suspension of wet material of micro-fibrillated cellulose ("CELISH", Daicel FineChem Ltd.) in water was sprayed onto it at a rate of 12 g/minute and then 160 g of an aqueous solution of sodium carmellose (CMC Daicel, Daicel FineChem Ltd.) at 1% by weight was sprayed onto it at a rate of 5 g/minute for granulation to thereby obtain particulate composition 5 according to the present invention. The resulting particulate composition 5 had the following values for physical properties: (1) an average particle size of 228 microns and (2) a water content of 1.24% by weight.

The resulting particulate composition 5 was then subjected to tableting at a tablet compression force of 10 kN with the simple tableting machine (HANDTAB-100, ICHI-HASHI-SEIKI Co., Ltd.) to thereby obtain a tablet having a diameter of 8.0 mm, R6.5 and a weight of 200 mg.

Example 5

Production of the Particulate Composition 6

350.6 g of erythritol (Erythritol T, Mitsubishi-Chemical Foods Corporation) and 19.9 g of guar gum (Guar gum RG 100, Mitsubishi-Chemical Foods Corporation) were charged to the fluidized-bed granulator (FL-LABO, Freund Corporation). 558 g of 5% suspension of wet material of micro-fibrillated cellulose ("CELISH", Daicel FineChem Ltd.) in water was sprayed onto it at a rate of 12 g/minute and then 160 g of an aqueous solution of sodium carmellose (CMC Daicel, Daicel FineChem Ltd.) at 1% by weight was sprayed onto it at a rate of 5 g/minute for granulation to thereby obtain particulate composition 6 according to the present invention. The resulting particulate composition 6 had the following values for physical properties: (1) an average particle size of 225 microns and (2) a water content of 1.39% by weight.

The resulting particulate composition 6 was then subjected to tableting at a tablet compression force of 10 kN with the simple tableting machine (HANDTAB-100, ICHI-HASHI-SEIKI Co., Ltd.) to thereby obtain a tablet having a diameter of 8.0 mm, R6.5 and a weight of 200 mg.

Example 6

Production of the Particulate Composition 7

350.6 g of erythritol (Erythritol I, Mitsubishi-Chemical Foods Corporation), 19.9 g of xanthan gum (Xanthan gum XG 800, Mitsubishi-Chemical Foods Corporation) and 4.4 g of sodium carmellose (CMC Daicel, Daicel FineChem Ltd.) were charged to the fluidized-bed granulator (FL-LABO, Freund Corporation). 558 g of 5% suspension of wet material of micro-fibrillated cellulose ("CELISH", Daicel FineChem Ltd.) in water was sprayed onto it at a rate of 12 g/minute and then 160 g of an aqueous solution of sodium carmellose (CMC Daicel, Daicel FineChem Ltd.) at 1% by weight was sprayed onto it at a rate of 5 g/minute for granulation to thereby obtain particulate composition 7 according to the present invention. The resulting particulate composition 7 had the following values for physical properties: (1) an average particle size of 259 microns and (2) a water content of 1.19% by weight.

The resulting particulate composition 7 was then subjected to tableting at a tablet compression force of 10 kN with the simple tableting machine (HANDTAB-100, ICHI-HASHI-SEIKI Co., Ltd.) to thereby obtain a tablet having a diameter of 8.0 mm, R6.5 and a weight of 200 mg.

In the following Examples 7 and 8, another water-soluble polymer was used instead of sodium carmellose used in Example 1 to produce the particulate compositions according to the present invention.

Example 7

Production of the Particulate Composition 8

396.8 g of the particulate composition obtained in Comparative Example 1 was charged to the fluidized-bed granulator (FL-LABO, Freund Corporation), and 640 g of an aqueous solution of xanthan gum (Xanthan gum XG 800, Mitsubishi-Chemical Foods Corporation) at 0.5% by weight was sprayed onto it at a rate of 5 g/minute for granulation to thereby obtain a particulate composition 8 according to the present invention. The resulting particulate composition 8 had the following values for physical properties: (1) an average particle size of 385 microns and (2) a water content of 0.88% by weight.

The resulting particulate composition 8 was then subjected to tableting at a tablet compression force of 8 kN with the simple tableting machine (HANDTAB-100, ICHI- HASHI-SEIKI Co., Ltd.) to thereby obtain a tablet having a diameter of 8.0 mm, R6.5 and a weight of 200 mg.

Example 8

Production of the Particulate Composition 9

396.8 g of the particulate composition obtained in Comparative Example 1 was charged to the fluidized-bed granulator (FL-LABO, Freund Corporation), and 640 g of an aqueous solution of sodium alginate (KIMICA ALGIN, KIMICA Corporation) at 0.5% by weight was sprayed onto it at a rate of 5 g/minute for granulation to thereby obtain a particulate composition 9 according to the present invention. The resulting particulate composition 9 had the following values for physical properties: (1) an average particle size of 381 microns and (2) a water content of 1.01% by weight.

The resulting particulate composition 9 was then subjected to tableting at a tablet compression force of 8 kN with the simple tableting machine (HANDTAB-100, ICHI-HASHI-SEIKI Co., Ltd.) to thereby obtain a tablet having a diameter of 8.0 mm, R6.5 and a weight of 200 mg.

Comparative Example 3

9.92 g of the particulate composition obtained in Comparative Example 1 and 0.08 g of xanthan gum (Xanthan gum XG 800, Mitsubishi-Chemical Foods Corporation) were mixed to obtain a composition. The resulting composition was then subjected to tableting at a tablet compression force of 8 kN with the simple tableting machine (HAND-TAB-100, ICHIHASHI-SEIKI Co., Ltd.) to thereby obtain a tablet having a diameter of 8.0 mm, R6.5 and a weight of 200 mg, wherein a small amount of calcium stearate (Taihei Chemical Industrial Co. Ltd.) had been applied in advance to the mortar inner surface, and the surfaces of the upper-pestle and the lower-pestle in the above tableting machine.

Comparative Example 4

9.92 g of the particulate composition obtained in Comparative Example 1 and 0.08 g of sodium alginate (KIMICA ALGIN, KIMICA Corporation) were mixed to obtain a composition. The resulting composition was then subjected to tableting at a tablet compression force of 8 kN with the simple tableting machine (HANDTAB-100, ICHIHASHI-SEIKI Co., Ltd.) to thereby obtain a flat with bevel-edge tablet having a diameter of 8.0 mm, R6.5 and a weight of 200 mg, wherein a small amount of calcium stearate (Taihei Chemical Industrial Co. Ltd.) had been applied in advance to the mortar inner surface, and the surfaces of the upper-pestle and the lower-pestle in the above tableting machine.

Example 9

Production of the Particulate Composition 10

160.2 g of xylitol (Xilite fine powder, Mitsubishi Shoji Foodtech Co., Ltd), 19.8 g of crystalline cellulose (CEOLUS KG-802, Asahi Kasei Chemicals Corp.) and 19.8 g of sodium carmellose (CMC Daicel, Daicel FineChem Ltd.) were charged to the fluidized-bed granulator (FL-LABO, Freund Corporation). 50 g of an aqueous solution of sodium carmellose (CMC Daicel, Daicel FineChem Ltd.) at 0.4% by weight was sprayed onto it at a rate of 5 g/minute for granulation to thereby obtain particulate composition 10 according to the present invention. The resulting particulate composition 10 had the following values for physical properties: (1) an average particle size of 233 microns and (2) a water content of 1.04% by weight.

The resulting particulate composition 10 was then subjected to tableting at a tablet compression force of 12 kN with the simple tableting machine (HANDTAB-100, ICHI-HASHI-SEIKI Co., Ltd.) to thereby obtain a tablet having a diameter of 8.0 mm, R6.5 and a weight of 200 mg.

In the following Example 10, the particulate composition according to the present invention was produced using mannitol instead of xylitol used in Example 9.

Example 10

Production of the Particulate Composition 11

150.0 g of mannitol (Pearlitol, Roquette Japan), 30.0 g of crystalline cellulose (CEOLUS KG-802, Asahi Kasei Chemicals Corp.) and 20.0 g of sodium carmellose (CMC Daicel, Daicel FineChem Ltd.) were charged to the fluidized-bed granulator (FL-LABO, Freund Corporation). 250 g of an aqueous solution of sodium carmellose (CMC Daicel, Daicel FineChem Ltd.) at 0.4% by weight was sprayed onto it at a rate of 5 g/minute for granulation to thereby obtain particulate composition 11 according to the present invention. The resulting particulate composition 11 had the following values for physical properties: (1) an average particle size of 183 microns and (2) a water content of 2.33% by weight.

The resulting particulate composition 11 was then subjected to tableting at a tablet compression force of 12 kN with the simple tableting machine (HANDTAB-100, ICHI-HASHI-SEIKI Co., Ltd.) to thereby obtain a tablet having a diameter of 8.0 mm, R6.5 and a weight of 200 mg.

In the following Examples 11 and 12, the particulate compositions according to the present invention was produced using isomalt as the sugar alcohol and sodium carmellose as the water-soluble polymer.

Example 11

Production of the Particulate Composition 12

368.0 g of isomalt (GalenIQ, BENEO Corporation) was charged to the fluidized-bed granulator (FL-LABO, Freund Corporation), and 640 g of 5% suspension of wet material of micro-fibrillated cellulose ("CELISH", Daicel FineChem Ltd.) in water was sprayed onto it at a rate of 12 g/minute for granulation to thereby obtain particulate composition.

396.8 g of the resulting particulate composition was charged to the fluidized-bed granulator (FL-LABO, Freund Corporation), and 320 g of an aqueous solution of sodium carmellose (CMC Daicel, Daicel FineChem Ltd.) at 1.0% by weight was sprayed onto it at a rate of 5 g/minute for granulation to thereby obtain a particulate composition 12 according to the present invention. The resulting particulate composition 12 had the following values for physical properties: (1) an average particle size of 372 microns and (2) a water content of 5.82% by weight.

The resulting particulate composition 12 was then subjected to tableting at a tablet compression force of 6 kN with the simple tableting machine (HANDTAB-100, ICHI-HASHI-SEIKI Co., Ltd.) to thereby obtain a tablet having a diameter of 8.0 mm, R6.5 and a weight of 200 mg.

Example 12

Production of the Particulate Composition 13

396.8 g of isomalt (GalenIQ, BENEO Corporation) was charged to the fluidized-bed granulator (FL-LABO, Freund Corporation), and 320 g of an aqueous solution of sodium carmellose (CMC Daicel, Daicel FineChem Ltd.) at 1.0% by weight was sprayed onto it at a rate of 5 g/minute for granulation to thereby obtain particulate composition 13 according to the present invention. The resulting particulate composition 13 had the following values for physical properties: (1) an average particle size of 324 microns and (2) a water content of 5.73% by weight.

The resulting particulate composition 13 was then subjected to tableting at a tablet compression force of 6 kN with the simple tableting machine (HANDTAB-100, ICHI-HASHI-SEIKI Co., Ltd.) to thereby obtain a tablet having a diameter of 8.0 mm, R6.5 and a weight of 200 mg.

Example 13

Production of the Particulate Composition 14

160.0 g of xylitol (Xilite fine powder, Mitsubishi Shoji Foodtech Co., Ltd) and 20.0 g of crystalline cellulose (CEOLUS KG-802, Asahi Kasei Chemicals Corp.) were charged to a centrifugal tumbling granulator (CF-LABO, Freund Corporation). After the rotation was started at 300 rpm, 20.0 g of sodium carmellose (CMC Daicel, Daicel FineChem Ltd.) was charged little by little while 30 g of water was sprayed onto it at a rate of 3 g/minute for granulation to thereby obtain particulate composition 14 according to the present invention. The resulting particulate composition 14 had the following values for physical properties: (1) an average particle size of 431 microns and (2) a water content of 2.12% by weight.

The resulting particulate composition 14 was then subjected to tableting at a tablet compression force of 12 kN with the simple tableting machine (HANDTAB-100, ICHI-HASHI-SEIKI Co., Ltd.) to thereby obtain a tablet having a diameter of 8.0 mm, R6.5 and a weight of 200 mg.

Example 14

Production of the Easy-to-Take Solid Preparation 1

15.7 g of the particulate composition obtained in Example 2, 4.0 g of vitamin C (Eisai Food Chemicals), 0.2 g of aspartame (Aspartame, AJINOMOTO HEALTHY SUPPLY CO., INC.) and 0.1 g of calcium stearate (Taihei Chemical Industrial Co. Ltd.) were mixed to obtain a composition. The resulting composition was then subjected to tableting at a tablet compression force of kN with the simple tableting machine (HANDTAB-100, ICHIHASHI-SEIKI Co., Ltd.) to thereby obtain a tablet (the easy-to-take solid preparation) having a diameter of 8.0 mm, R6.5 and a weight of 200 mg.

Comparative Example 5

15.7 g of the particulate composition obtained in Comparative Example 1, 4.0 g of vitamin C (Eisai Food Chemicals), 0.2 g of aspartame (Aspartame, AJINOMOTO HEALTHY SUPPLY CO., INC.) and 0.1 g of calcium stearate (Taihei Chemical Industrial Co. Ltd.) were mixed to obtain a composition. The resulting composition was then subjected to tableting at a tablet compression force of 8 kN with the simple tableting machine (HANDTAB-100, ICHI-HASHI-SEIKI Co., Ltd.) in order to obtain a tablet having a diameter of 8.0 mm, R6.5 and a weight of 200 mg. However, strong tableting-obstacles occurred and inhibited from producing the tablet.

[Evaluation of Hardness and Slipperiness]

The measured values of Hardness and Slipperiness of Examples 1-14 and Comparative Examples 1-5 are shown in Table 1 below.

TABLE 1

| | Tablet Compression Force (kN) | tableting-obstacles | Tablet Hardness (N) | Slipperiness (g) |
|---|---|---|---|---|
| Comparative Example 1 | 8 | Yes | 42 | 259 |
| Comparative Example 1 | 8 | Yes | 50 | 170 |
| Example 1 | 8 | No | 87 | 81 |
| Example 2 | 8 | No | 160 | 359 |
| Example 3 | 8 | No | 177 | 40 |
| Example 4 | 10 | No | 138 | 17 |
| Example 5 | 10 | No | 138 | 18 |
| Example 6 | 10 | No | 135 | 13 |
| Example 7 | 8 | No | 80 | 164 |
| Example 8 | 8 | No | 73 | 95 |
| Comparative Example 3 | 8 | Yes | 84 | 244 |
| Comparative Example 4 | 8 | present | 88 | 189 |
| Example 9 | 12 | No | 135 | 8 |
| Example 10 | 12 | No | 83 | 13 |
| Example 11 | 6 | No | 187 | 56 |
| Example 12 | 6 | No | 181 | 77 |
| Example 13 | 12 | No | 130 | 9 |
| Example 14 | 8 | No | 82 | 28 |
| Comparative Example 5 | 8 | Yes | N.D. | — |

According to the results shown in Table 1, it is demonstrated that the tablets (Examples 1-6, 9-13) according to the present invention produced using the particulate composition 2-7, 10-14 obtained by spraying sodium carmellose as the water-soluble polymer for granulation have excellent moldability so that a tablet with high hardness can be produced without occurring the tablet-obstacles during tableting, when compared to the tablet (Comparative Example 1) produced using the particle composition 1 without comprising sodium carmellose or the tablet (Comparative Example 2) produced using the mixture of the particle composition 1and sodium carmellose. Since the tablet-obstacles occurred at a tablet compression force of 8 kN, the tablet hardness of Comparative Examples 1 and 2 could not be increased even the tablet compression force was increased to more than 8 kN.

It is also demonstrated that the tablets according to the present invention have more excellent slipperiness than the tablet (Comparative Example 2) produced using the mixture of particulate composition 1 and sodium carmellose.

It is further demonstrated that the tablet (Example 14) produced using the mixture of the particulate composition 3 and the functional components has excellent slipperiness and moldability so that a tablet with high hardness can be produced without occurring of the tablet-obstacles during tableting, when compared to the tablet (Comparative Example 5) produced using the mixture of the particulate composition 1 and the functional components or the tablet (Comparative Example 1) produced using the particle composition 1.

It is further demonstrated that the tablets (Examples 7 and 8) produced using the particulate compositions 8 and 9 obtained by spraying the aqueous solution of xanthan gum and sodium alginate, respectively, for granulation have excellent slipperiness and moldability so that a tablet with a high hardness can be produced without occurring of the tablet-obstacles during tableting, when compared to the tablets (Comparative Examples 3 and 4) produced just by mixing the particulate composition 1 and the above water-soluble polymers.

It is also demonstrated that the tablet (Example 12) that were produced using the particulate composition 13 obtained using only isomalt as the sugar alcohol and sodium carmellose as the water-soluble polymer but not the water-insoluble polymer has excellent slipperiness and moldability without occurring of the tablet-obstacles during tableting.

Example 15

Production of the Easy-to-Take Solid Preparation 2

5.7 g of lactose (FlowLac90, MEGGLE JAPAN CO., LTD.), 2.0 g of hydroxypropylcellulose (HPC-SSL-SFP, NIPPON SODA CO., LTD.), 12.0 g of vitamin C (Eisai Food Chemicals), 0.2 g of aspartame (Aspartame, AJINOMOTO HEALTHY SUPPLY CO., INC.) and 0.1 g of calcium stearate (Taihei Chemical Industrial Co. Ltd.) were mixed to obtain a composition. The resulting composition was then subjected to tableting at a tablet compression force of 2 kN with the simple tableting machine (HANDTAB-100, ICHIHASHI-SEIKI Co., Ltd.) to thereby obtain an inner core tablet having a diameter of 10.0 mm, R14 and a weight of 400 mg.

400 mg g of the inner core tablet and the particulate composition obtained in Example 2 were subjected to tableting at a tablet compression force of 8 kN with the simple tableting machine (HANDTAB-100, ICHIHASHI-SEIKI Co., Ltd.) to thereby obtain a nucleated tablet (the easy-to-take solid preparation) having a diameter of 12.0 mm, R14 and a weight of 600 mg, wherein a small amount of calcium stearate (Taihei Chemical Industrial Co. Ltd.) had been applied in advance to the mortar inner surface, and the surfaces of the upper-pestle and the lower-pestle in the above tableting machine. The taste-masking effect of the resulting tablet was measured to be 48.8 seconds.

Comparative Example 6

17.9 g of lactose (FlowLac90, MEGGLE JAPAN CO., LTD.), 2.0 g of hydroxypropylcellulose (HPC-SSL-SFP, NIPPON SODA CO., LTD.) and 0.1 g of calcium stearate (Taihei Chemical Industrial Co. Ltd.) were mixed to obtain a composition. The resulting composition was then subjected to tableting at a tablet compression force of 6 kN with the simple tableting machine (HANDTAB-100, ICHIHASHI-SEIKI Co., Ltd.) to thereby obtain a tablet having a diameter of 12.0 mm, R14 and a weight of 600 mg.

Comparative Example 7

5.7 g of lactose (FlowLac90, MEGGLE JAPAN CO., LTD.), 2.0 g of hydroxypropylcellulose (HPC-SSL-SFP, NIPPON SODA CO., LTD.), 12.0 g of vitamin C (Eisai Food Chemicals), 0.2 g of aspartame (Aspartame, AJINOMOTO HEALTHY SUPPLY CO., INC.) and 0.1 g of calcium stearate (Taihei Chemical Industrial Co. Ltd.) were mixed to obtain a composition. The resulting composition was then subjected to tableting at a tablet compression force of 10 kN with the simple tableting machine (HANDTAB-100, ICHIHASHI-SEIKI Co., Ltd.) to thereby obtain a tablet having a diameter of 10.0 mm, R14 and a weight of 400 mg. Hardness of the resulting tablet was 96 N.

[Evaluation of Hardness and Slipperiness]

Tablet hardness and slipperiness of the tablets of Example 15 and Comparative Example 6 are shown in Table 2. It demonstrates that the nucleated tablet coated with the particulate composition 3 according to the present invention shows an excellent slipperiness when compared to the tablet having the same shape (Comparative Example 6).

TABLE 2

|  | Tablet Hardness (N) | Slipperiness (g) |
|---|---|---|
| Example 15 | 117 | 92 |
| Comparative Example 6 | 120 | 892 |

BRIEF DESCRIPTION OF DRAWINGS

[Evaluation of Elution Time]

Fig.1 shows the results of elution test of the tablets obtained in Example 15 and Comparative Example 7. They demonstrate that the elution of the functional component (vitamin C) comprised in the core tablet of the nucleated tablet coated with the particulate composition 3 according to the present invention is delayed so as to show the taste-masking effect. Thus, the nucleated tablet coated with the particulate composition according to the present invention has excellent effect for masking the taste of the core tablet in addition to excellent slipperiness.

INDUSTRIAL APPLICABILITY

The present invention significantly contributes to research and development of the composition for the outer layer of the easy-to-take solid preparation and the like.

The invention claimed is:

1. A particulate composition for a solid preparation, comprising a plurality of particles, wherein each particle comprises a sugar alcohol, at least one kind of a water-soluble polymer and a water-insoluble polymer,
   wherein the water-insoluble polymer is micro-fibrillated cellulose having an average fiber length of 0.01-2 mm and an average fiber diameter of 0.001-1 µm or crystalline cellulose, and wherein the surface of each particle is coated only with the water-soluble polymer.

2. The particulate composition according to claim 1, wherein the water-insoluble polymer is the micro-fibrillated cellulose.

3. The particulate composition according to claim 1, wherein the water-insoluble polymer is the crystalline cellulose.

4. The particulate composition according to claim 1, wherein the sugar alcohol comprises one or more selected from the group consisting of erythritol, xylitol, mannitol, sorbitol, lactitol, isomalt and maltitol.

5. The particulate composition according to claim 1, wherein the water-soluble polymer is selected from the group consisting of sodium carmellose, xanthan gum, sodium alginate, carrageenan, guar gum and gelatin.

6. The particulate composition according to claim 1, wherein the sugar alcohol is selected from the group consisting of erythritol, xylitol, isomalt and mannitol; the water-insoluble polymer is the micro-fibrillated cellulose or the crystalline cellulose; and the water-soluble polymer is sodium carmellose.

7. A method for the production of the particulate composition according to claim 1, comprising a step of spraying a liquid comprising the water-soluble polymer to a composition comprising at least the sugar alcohol with the micro-fibrillated cellulose or crystalline cellulose, so that the surface of each particle in the particulate composition is coated only with the water-soluble polymer.

8. A method for the production of the particulate composition according to claim 1, comprising a step of
investing powder of the water-soluble polymer into a composition comprising at least the sugar alcohol with the micro-fibrillated cellulose or crystalline cellulose, while spraying water onto the composition, so that the surface of each particle in the particulate composition is coated only with the water-soluble polymer.

9. A solid preparation comprising the particulate composition according to claim 1.

10. A solid preparation for foods or pharmaceuticals, wherein an inner core is coated with an outer layer consisting of the particulate composition according to claim 1.

11. A method for the production of the solid preparation according to claim 9, comprising only a step of compression-molding in a dry process.

12. A solid preparation, comprising the particulate composition obtained by the method for the production according to claim 7.

13. A solid preparation, comprising the particulate composition obtained by the method for the production according to claim 8.

14. A solid preparation for foods or pharmaceuticals, wherein an inner core is coated with the outer layer consisting of the particulate composition obtained by the method for the production according to claim 7.

15. A solid preparation for foods or pharmaceuticals, wherein an inner core is coated with the outer layer consisting of the particulate composition obtained by the method for the production according to claim 8.

16. The particulate composition according to claim 1, wherein a medicinal or active ingredient is not comprised.

* * * * *